United States Patent [19]
DesMarais et al.

[11] Patent Number: 4,892,536
[45] Date of Patent: Jan. 9, 1990

[54] ABSORBENT ARTICLE HAVING ELASTIC STRANDS

[75] Inventors: Thomas A. DesMarais; Mary E. Freeland, both of Norwood; William J. Moore, Cincinnati, all of Ohio

[73] Assignee: The Procter & Gamble Company, Cincinnati, Ohio

[21] Appl. No.: 240,149

[22] Filed: Sep. 2, 1988

[51] Int. Cl.[4] ........................................ A61F 13/16
[52] U.S. Cl. .................................................. 604/385.2
[58] Field of Search ............ 604/350, 351, 355, 385.1, 604/385.2, 392–395

[56] References Cited

U.S. PATENT DOCUMENTS

| 2,004,088 | 6/1935 | Alsop | 604/397 |
| 2,532,029 | 11/1950 | Medoff | 604/401 |
| 2,538,758 | 1/1951 | Bricmont | 604/347 |
| 2,690,749 | 10/1954 | Nelson | 128/287 |
| 3,103,930 | 9/1963 | Collett et al. | 604/359 |
| 3,421,160 | 1/1969 | Koornwinder | 604/348 |
| 3,532,093 | 10/1970 | Lovret | 128/286 |
| 3,593,716 | 7/1971 | Vogt | 604/366 |
| 3,729,004 | 4/1973 | Burger | 604/401 |
| 3,890,973 | 6/1975 | Davis et al. | 604/355 |
| 4,662,877 | 5/1987 | Williams | 604/385.1 |
| 4,676,785 | 6/1987 | Battista | 604/369 |
| 4,695,278 | 9/1987 | Lawson | 604/385 A |
| 4,704,116 | 11/1987 | Enloe | 604/385 A |
| 4,731,065 | 3/1988 | Yamada | 604/355 |
| 4,834,737 | 5/1989 | Khan | 604/385.1 |

FOREIGN PATENT DOCUMENTS 2561078 9/1985 France .
8800010 1/1988 World Int. Prop. O. ....... 604/385.2

Primary Examiner—C. Fred Rosenbaum
Assistant Examiner—Mark O. Polutta
Attorney, Agent, or Firm—Larry L. Huston; John M. Pollaro; Frederick H. Braun

[57] ABSTRACT

A disposable absorbent article, such as a diaper, having a liquid impervious backsheet, a urine pervious liner, and absorbent core intermediate the backsheet and liner is disclosed. The liner has a passageway to allow communication of solid waste materials to the core, thereby isolating such waste from the skin of the wearer. The liner is longitudinally contracted by elastic strands disposed longitudinally nonadjacent the passageway, improving the fit of the article to the wearer without sacrificing leakage protection and allowing various sections of the article to assume independent functions.

14 Claims, 2 Drawing Sheets

ABSORBENT ARTICLE HAVING ELASTIC STRANDS

TECHNICAL FIELD

The present invention relates to disposable absorbent articles, and more particularly to disposable absorbent articles having selectively placed elastic strands to enhance the fit of the article to the wearer.

BACKGROUND OF THE INVENTION

Several attempts within the art relating to disposable absorbent articles have been made to enhance the fit of the article to the wearer. A better fitting article provides more comfort for the wearer and can be adapted to isolate waste materials from the skin of the wearer. Fecal material which contacts the skin is often a source of epidermal irritation and makes cleaning of the wearer more difficult.

An attempt to overcome these problems is disclosed in U.S. Pat. No. 4,662,877 issued to Williams, May 5, 1987, which discloses a diaper having a urine impervious facing sheet with an aperture to allow waste materials to pass through the facing sheet into the absorbent portion of the diaper. The diaper has elastic strands in the facing sheet to urge it away from the underlying absorbent structure. However, Williams teaches applying the elastic strands longitudinally adjacent the large and convexly rectangular aperture. This arrangement makes sealing around the leg openings more difficult, and does not provide for alignment of the aperture relative to the anal opening.

SUMMARY OF THE INVENTION

It is an object of this invention to obviate aforementioned problems related to article fit and fecal material reposing against the skin of the wearer of a disposable absorbent article. The invention comprises a disposable absorbent article having a longitudinal axis and a urine impervious backsheet. The article also has a liner which is generally adjacent the skin of the wearer when the article is in use. The liner has a passageway to permit communication of waste materials through the liner. An absorbent core is disposed intermediate the liner and backsheet. The absorbent article also has a means for contracting the liner in the longitudinal direction and which is disposed substantially longitudinally nonadjacent the passageway. In a preferred embodiment the longitudinal contracting means comprises elastic strands.

BRIEF DESCRIPTION OF THE DRAWINGS

While the Specification concludes with Claims particularly pointing out and distinctly claiming the subject matter of the invention, it is believed the invention will be better understood from the following description taken in conjunction with the accompanying drawings wherein like parts are given the same reference numerals.

DETAILED DESCRIPTION OF THE INVENTION

A disposable article made according to the present is typically a diaper, but could also be a catamenial pad, a product for incontinent adults or any other execution known to those skilled in the art. The disposable article disclosed herein can be manufactured and prepared using methods and materials well known in commercial practice.

The diaper herein described is suitable for infants of either sex weighing from approximately 5 kg. to approximately 11 kg. It is understood that the diaper may be adapted to larger and smaller wearers by appropriate scaling of the components discussed below.

Figure 1:
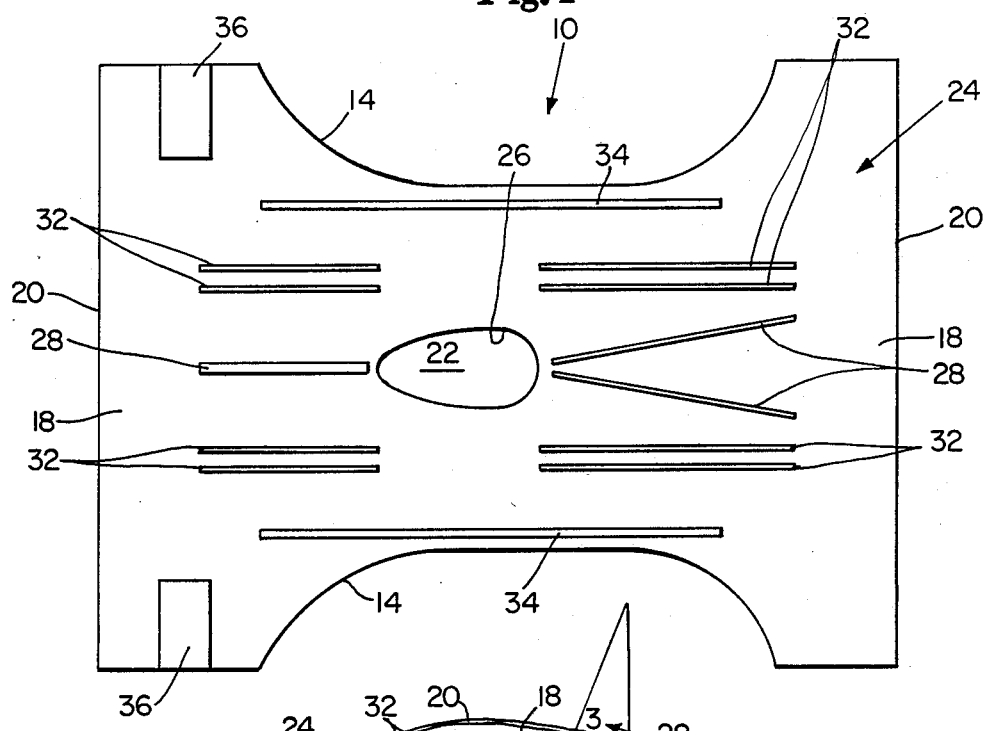
FIG. 1 is a top plan view of an embodiment of a disposable diaper made according to the present invention.

FIG. 1 is a top plan view of an unfolded and flattened diaper 10 having the basic components typical of such an absorbent article: a backsheet 12, an absorbent core 16, a liner 24 and a longitudinal contracting means associated with the liner 24.

The diaper 10 comprises a laminated structure having a generally hourglass shape in the flat, unfolded position. The diaper 10 is generally symmetric about a longitudinal axis oriented from the front to back of the diaper 10, which axis is generally aligned with the machine direction of the diaper 10 during manufacture. A transverse axis is orthogonal to the longitudinal axis of the diaper 10 and intersects the longitudinal axis at or near the midpoint of diaper 10. As used herein, the front and rear portions of the diaper 10 are defined by and coterminous of the transverse axis and are generally the portions of the diaper 10 disposed to the front and rear of the diaper 10 as observed by the wearer.

The diaper 10 comprises a backsheet 12 which is preferably urine impervious and flexible. An opaque polymer sheet is often utilized. The backsheet 12 provides a chassis for assembly of the diaper 10 about the arcuate posterior of the wearer and holds the other diaper components hereinafter discussed.

The backsheet 12 is sized to be drawn between the legs of the wearer and sealed with elastic leg cuffs 34. The backsheet 12 is fastened about the waist using tapes 36 disposed at the back of the backsheet 12. A diaper 10 generally constructed according to the teachings of U.S. Pat. No. 3,860,003, issued to Buell, Jan. 14, 1975, and incorporated herein by reference is suitable.

A low density polyethylene backsheet 12 about 0.01 mm. to about 0.3 mm. thick is typical, with a thickness of about 0.03 mm. being preferred. A backsheet 12 having a longitudinal dimension of about 45 cm., a transverse dimension between either end of the longitudinal edges 14 of about 32 cm. and a transverse dimension at the center of the longitudinal edges 14 of about 20 cm. is suitable.

Juxtaposed with the backsheet 12, towards the skin of the wearer, is a urine absorbent core 16, which is generally soft, conformable and compliant. The core 16 comprises any urine absorbent material such as cellulose fibers, and is typically comminuted cellulosic fiber, often known as air felt. The core 16 may further comprise absorbent gelling polyacrylate materials to increase the capacity of core 16.

The core 16 is designed to absorb and retain the expected volume of liquid discharge for the article's intended use, wear time and wearer capacity. For the embodiment described herein, the core 16 should preferably have a minimum capacity of about 300 ml. to accommodate the expected urine discharges of the wearer. The core 16 may be generally rectangular, having two opposed faces about 35 cm. to about 40 cm. long and about 10 to about 15 cm. wide, although it will be apparent to one skilled in the art that other shapes or sizes could be used as well. The core 16 is longitudinally shorter than the backsheet 12 to provide a free margin 18 at each transverse edge 20 of the diaper 10.

The core 16 may be integrally affixed to the backsheet 12, may be peripherally affixed to the backsheet 12, or not affixed to the backsheet 12. If it is desired to affix the core 16 to the backsheet 12, affixing may be accomplished with any suitable urine stable adhesive, such as Century 5227 made by Century Adhesives of Columbus, Ohio.

It is preferable that the core 16 remain intact, in position and not clump, break up or experience undue variations in thickness, otherwise discomfort to the wearer and uneven absorption capacity might result. To provide stability to the core 16, and prevent such disturbances to core uniformity from occurring, the core 16 may be tightly covered with an envelope 22. The envelope 22 may cover either or both faces of the core 16 and be peripherally or integrally affixed to the backsheet 12, using the aforementioned adhesive. The envelope 22 may be made of any urine pervious material, such as spun bonded or carded polyethylene or polypropylene fabric having a caliper of about 0.25 mm. and a basis weight of about 16.7 gm. per sq. m.

Juxtaposed with the absorbent core 16 (or envelope 22, if included), towards the wearer, is an inelastic urine pervious, generally nonabsorbent liner 24. The liner 24 is preferably soft, conformable and nonirritating to the skin. The liner 24 may be made of nonwoven fabric, such as the envelope 22 material described above, or may be a formed film polyolefinic sheet having perforations for the transmission of urine to the absorbent core 16. As used herein, a liner 24 is considered urine pervious if it has any zone or portion of the liner 24 which enables urine to pass therethrough, even though a portion or zone of the liner 24 may be urine impervious.

The liner 24 may generally correspond in size and shape to the backsheet 12. The liner 24 is at least partially, and preferably fully, peripherally affixed to the backsheet 12, laminating the core 16 intermediate the liner 24 and backsheet 12. The liner 24 may be affixed to the backsheet 12 using any well known method such as adhesive, thermal sealing or ultrasonic welding. The liner 24 is considered to be affixed to the backsheet 12 if the liner 24 is directly attached to the backsheet 12 (as shown) or indirectly attached to the backsheet 12 through a separate component.

Associated with the liner 24 is a passageway 26 which permits communication of waste materials, particularly including but not limited to solid fecal materials, through the liner 24 and into the region of the absorbent core 16, thereby isolating the waste materials from the skin of the wearer. In a preferred embodiment, the passageway 26 takes the form of an aperture. As used herein a passageway is any opening through the liner 24 which is sufficient to permit fecal material to pass through the liner 24 without significant obstruction. As used herein the term aperture includes but is not limited to holes, slits or any combination thereof. Preferably the aperture is an oblong hole having a doubly convex shape.

The size of the passageway 26 is a balance between the minimum size necessary to accommodate variations in the placement of the anus relative to the perineum and various cross sections of solid fecal material, while minimizing undue skin contact with the waste material. It is preferred that the passageway 26 have a greater longitudinal than transverse dimension to ensure registration with the anal opening when the diaper 10 is placed in various longitudinal alignments on the infant.

An aperture having a longitudinal dimension of about 5.0 cm. to about 6.5 cm., and a transverse dimension between about 3.5 cm. and about 6.0 cm. is suitable. The aperture is generally transversely centered on the liner 24 and longitudinally offset at least about 2 cm. towards the back of the diaper 10.

Associated with the liner 24 is a means for causing contraction of the liner 24 in the longitudinal direction. The contracting means preferably remains elastic from the time the diaper 10 is manufactured until the diaper 10 is discarded and is capable of being selectively positioned on the liner 24.

For the inelastic liner 24 described above, the contracting means is preferably provided by rubber strands 28, which function as tensors, oriented with a component parallel to the longitudinal axis of the diaper 10. As used herein, the elastic strands 28 may be of any cross section and have a substantially greater length than transverse dimension. Elastic strands 28 made of natural rubber and having an untensioned rectangular cross section of about 2.4 mm. to about 6.4 mm. by about 0.18 mm. is suitable. Fulflex 9411 strands made by the Fulflex Company of Scotland Neck, North Carolina have been found to work well. Typically, the elastic strands 28 are prestretched, then affixed to the diaper 10 using a suitable adhesive, as generally disclosed in U.S. Pat. No. 4,081,301, issued to Buell, Mar. 28, 1978 and incorporated herein by reference.

The liner 24 preferably has an uncontracted area, referred to as a free margin 18, disposed at each end of the diaper 10 intermediate the transverse edge of the core 16 and the transverse edge 20 of the backsheet 12. The elastic strands 28 referably do not extend into or contract the free margin 18, and are preferably coterminous of the core 16. This arrangement reduces wrinkling and contraction of the free margin 18 areas, providing more comfort to the user and reducing leakage around the waist of the diaper 10. Also, by making the contracted portion of the liner 24 shorter than the backsheet 12, the diaper 10 will bow concave towards the liner 24 when the liner 24 and backsheet 12 are affixed, creating a frame suitable to accommodate the arcuate posterior of the wearer. For a backsheet 12 having a length of about 45 cm., as described above, a liner 24 having a longitudinally contracted dimension ranging from about 23 cm. to about 36 cm. is typically suitable.

The longitudinal contracting means is disposed longitudinally nonadjacent the passageway 26. As used herein, longitudinally nonadjacent the passageway 26 refers to any portion of the liner 24 which is displaced from the passageway 26 towards either transverse edge 20 of the diaper 10. Alternatively stated, any point on the liner 24 through which a line parallel to the transverse axis can be drawn without intersecting the passageway 26 is longitudinally nonadjacent the passageway 26. It is to be understood that an elastic strand 28 which is laterally nonadjacent the passageway 26 may also have a portion laterally adjacent the passageway 26, and fall within the scope of the claimed invention.

The contracting means may be disposed transversely adjacent the passageway 26. As used herein transversely adjacent the passageway 26 refers to any portion of the liner which is displaced from the passageway directly towards either transverse edge 20 the diaper 10. Alternatively stated, any point on the liner 24 through which a line can be drawn parallel to the longitudinal axis and intersecting the passageway 26 is transversely adjacent the passageway 26.

Without being limited to any theory of operation, it is believed this arrangement causes the liner 24 to better conform to the complex curvatures of the buttocks of the wearer and obviates longitudinal collapse of the passageway 26. Furthermore, it is believed this arrangement aligns the passageway 26 to the anal opening of the wearer and provides for sealing of the liner 24 against the skin of the wearer. Preferably both a front and a rear liner contracting means are provided, one each side of the passageway 26 and associated with the liner 24, although a diaper 10 with either a front or rear liner contracting means will provide at least a portion of the aforementioned benefits.

Figure 2:
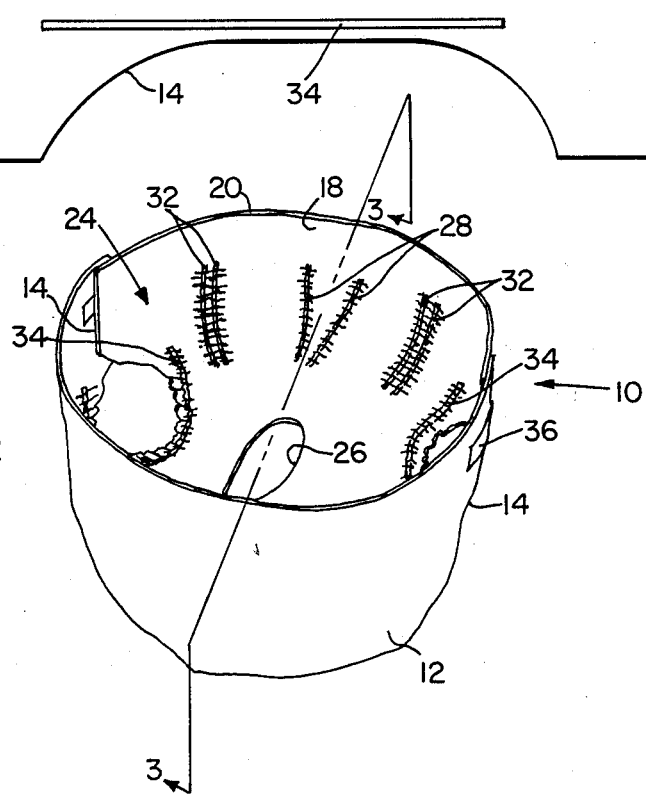
FIG. 2 is a perspective view of the diaper shown in FIG. 1, looking towards the front of the diaper when it is assembled on a wearer, not shown, in the standing position.

A liner contracting means for the rear portion of liner 24, preferably comprises one or more elastic strands 28, laterally centered and aligned generally parallel to the longitudinal axis of the diaper 10. Referring to FIG. 2, the rear elastic strand 28 pulls vertically upwardly on the back of the liner 24 when the diaper 10 is being worn by a wearer in the standing position. Also, the rear elastic strand 28 urges the back panel of the liner 24 into the gluteal groove, which tends to prevent solid waste material from migrating into this region of the wearer's body.

A liner contracting means for the front portion of liner 24 preferably comprises one or more elastic strands 28 and preferably provides a longitudinal vector balance against the opposite pull of the rear elastic strands 28. A liner contracting means for the front portion of liner 24 having elastic strands 28 disposed in a V-shape with the vertex oriented towards the passageway 26 and opening towards the front of the diaper 10 is preferred. This arrangement has a substantial component of elasticity in the longitudinal direction, balancing the opposing pull of the rear portion contracting means and providing the alignment and sealing functions discussed above. In a manner similar to that described above, as shown in FIG. 2, the front strands 28 pull vertically upward on the front panel of the diaper 10 when assembled about a wearer in the standing position.

The included angle of the V-shaped liner front portion contracting means should be small enough to provide a longitudinally forward pull, yet wide enough that the strands 28 not abrade or irritate the genitalia, and particularly be wide enough to accommodate the male scrotum. For this reason, the elastic strands 28 may terminate without intersection at the vertex of the "V" or intersect in an arcuate pattern, such as a U-shape, and still fall within the scope of the present invention. A liner front portion front contracting means having an included angle of about 20 to about 90 degrees between strands 28 is suitable, although the angle may vary according to the lateral spacing of the strands 28.

The strands 28 should not be extended into the free margin 18 area of the diaper 10, otherwise distortion of the waist area occurs when the diaper 10 is applied to the wearer. Similarly, the strands 28 should not be too close to the passageway 26, otherwise it may contract or contort into an irregular shape and diminish liner 24 contact with the skin. Conversely, the strands 28 should not be too short, or disposed too far from the passageway 26, otherwise alignment of the passageway 26 and lifting of the liner 24 from the core 16 are difficult to achieve.

Front and rear elastic strands 28 having a modulus of about 125,000 kg. per sq. m. at an elongation of about 100 to about 200 percent, transversely adjacent the passageway 26 and having an uncontracted elongation of about 125 percent to about 200 percent, typically about 175 percent, a length of about 16.5 cm. in the front, and about 14.6 cm. in the rear, has been found to work well for the embodiment described herein. If desired, the urine acquiring zone of the liner 24 may be adhered to the core 16 to promote transmission of the urine through the liner 24.

Figure 3:
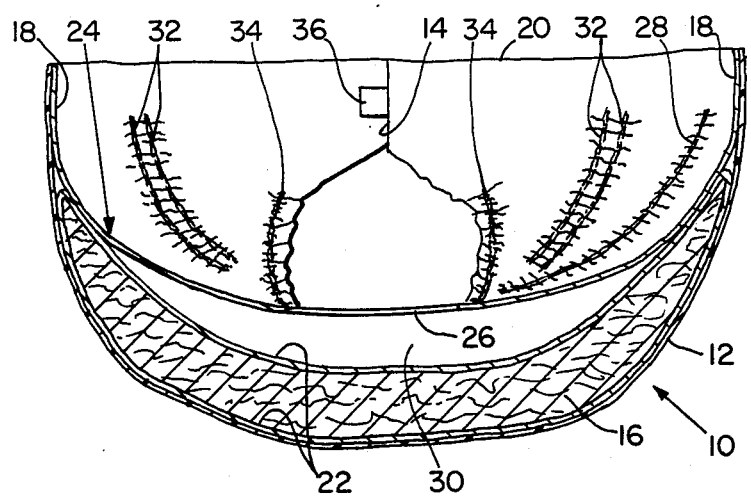
FIG. 3 is a vertical sectional view taken along line 3—3 of FIG. 2 showing the void space between the liner and core.

As shown in FIG. 3, when worn, ideally the longitudinally contracted diaper liner 24 will closely adhere to the wearer, while the larger radius of curvature of the absorbent core 16 will allow the core 16 to fall away from the liner 24 and create a void space 30 therebetween. The void space 30 may function to collect waste materials and isolate the collected materials from the wearer, preventing epidermal irritation.

The volume of void space 30 is not critical, so long as at least about 90 gm. of fecal material can be accommodated. Likewise, the shape of void space 30 is not critical, and indeed will be irregular. Preferably the liner 24 is not affixed to the core 16 near the vicinity of the passageway, otherwise the void space 30 capacity may be substantially reduced.

It will be apparent to one skilled in the art that various modifications may be made to the first embodiment disclosed above. For example, the void space 30 between the liner 24 and core 16 may be enhanced by adding secondary elastic strands 32, illustrated in FIGS. and 2, which act as tensors to longitudinally contract the liner 24. The secondary elastic strands 32 are disposed in a generally longitudinal orientation, and are longitudinally nonadjacent the passageway 26. The secondary strands lift the sides of the liner 24 away from the core 16 and thereby may enhance separation and isolation of solid fecal material from the wearer.

The secondary strands are preferentially symmetrically disposed about the longitudinal and transverse diaper axes, having one group of strands in each quadrant of the liner 24. This arrangement also promotes lateral tensioning of the liner 24 and greater opening of the passageway 26. The secondary elastic strands 32 preferably impart less contraction, or differential from the free length, to the liner 24 than the front and rear strands 28, as it is believed this arrangement lifts the center of the liner 24 to better conform to the shape of the buttocks. Typically, four elastic strands in each group of secondary strands having the same lengths as the aforementioned transversely adjacent front and rear elastic strands 28 and having from about 100 percent to about 200 percent, typically 150 percent elongation in the uncontracted state are suitable.

It will be apparent to one skilled in the art that other sizes and shapes of apertures are feasible to permit waste materials to pass through the liner 24. For example, a diamond shaped aperture (not shown) of the aforementioned dimensions and having the corners oriented in the longitudinal and transverse directions is suitable. An aperture such as a slit (not shown) having a longitudinal dimension ranging about 4.0 cm. to about 6.0 cm. and a transverse dimension of about 0.5 cm. may be used. If the diaper 10 is to be scaled for a larger infant, a larger passageway 26 disposed closer to the rear of the diaper 10 may be desirable. All such passageways 26 are within the scope of the present invention.

If desired, the portion of the liner 24 near the passageway 26 may be reinforced to prevent tearing or wrinkling. Reinforcement may be accomplished by providing a double thickness of the liner material in a band adjacent and concentric of the passageway 26 and having a radial dimension of about 1.0 cm. to about 2.0 cm.

If desired, a transverse contracting means may be incorporated into the liner 24 of any embodiment described above. The magnitude of the transverse contraction is not critical, but may be used to generally neutralize any lateral necking which occurs due to the longitudinal contraction. For example, elastic strands 28 having any nonlongitudinal orientation, such as the V-shape of FIG. 1, provides transverse contraction.

It will be apparent to those skilled in the art that many other modifications may be made without departure from the spirit and scope of the invention.

What is claimed is:

1. A disposable absorbent article having a longitudinal axis, said article comprising:
   a urine impervious backsheet;
   a urine pervious liner having a front portion, a rear portion and at least one passageway adapted to permit waste materials to pass through said liner, said liner being at least partially peripherally affixed to said backsheet;
   an absorbent core intermediate said liner and said backsheet;
   a means for contracting said liner in the longitudinal direction, said contracting means being disposed substantially longitudinally nonadjacent said passageway and in the front portion of said liner; and
   a means for contracting said liner in the longitudinal direction, said contracting means being disposed substantially longitudinally nonadjacent said passageway and in the rear portion of said liner.

2. A disposable absorbent article having a longitudinal axis, said article comprising:
   a urine impervious backsheet;
   a urine pervious liner having a front portion, a rear portion and at least one passageway adapted to permit waste materials to pas through said liner, said liner being at least partially peripherally affixed to said backsheet;
   an absorbent core intermediate said liner and said backsheet; and
   at least one elastic strand disposed in said front portion and at least one elastic strand disposed in said rear portion, which elastic strands contract said liner in the longitudinal direction, said elastic strands being substantially longitudinally nonadjacent said passageway.

3. A disposable absorbent article according to claim 1 or 2 wherein said passageway is an aperture.

4. A disposable absorbent article according to claim 3 wherein said aperture has a greater longitudinal dimension than transverse dimension.

5. A disposable absorbent article according to claim 1 or 2 further comprising a means for transverse contraction of said liner.

6. A disposable absorbent article according to claim 5 wherein said means for transverse contraction of said liner comprises at least one elastic strand having a nonlongitudinal orientation.

7. A disposable absorbent article according to claim 6 wherein said liner has a front portion and a rear portion, said liner having more than one elastic strand disposed in said front portion and at least one elastic strand disposed in said rear portion.

8. A disposable absorbent article according to claim 7 having two elastic strands disposed in said front portion, said two elastic strands forming a V-shape, said V-shape having the vertex oriented towards said passageway.

9. A disposable absorbent article according to claim 8 wherein said elastic strands are transversely adjacent said passageway and further comprising a plurality of secondary elastic strands which contract said liner in the generally longitudinal direction, said secondary elastic strands being disposed substantially transversely and longitudinally nonadjacent said passageway.

10. A disposable absorbent article according to claim 9 wherein said secondary elastic strands contract said liner less than said transversely adjacent elastic strands contract said liner.

11. A disposable absorbent article according to claim 1 wherein said front portion contracting means and said rear portion contracting means are oriented at an angle of about 0° to about 45° relative to the longitudinal axis.

12. A disposable absorbent article according to claim 11 wherein both of said contracting means are oriented at an angle of about 10° to about 45° relative to the longitudinal axis.

13. A disposable absorbent article according to claim 2 wherein said front portion elastic strands and said rear portion elastic strands are oriented at an angle of about 0° to about 45° relative to the longitudinal axis.

14. A disposable absorbent article according to claim 13 wherein both of said elastic strands are oriented at an included angle of about 10° to about 45° relative to the longitudinal axis.

* * * * *

UNITED STATES PATENT AND TRADEMARK OFFICE
CERTIFICATE OF CORRECTION

PATENT NO.  : 4,892,536

DATED       : January 9, 1990

INVENTOR(S) : Thomas A. DesMarais, Mary E. Freeland, and William J. Moore

It is certified that error appears in the above-identified patent and that said Letters Patent is hereby corrected as shown below:

FACE OF PATENT

Attorney, Agent, or Firm - reads "Frederick H. Braun" should read --Fredrick H. Braun--.

IN THE SPECIFICATION

Column 2, line 7, after "present" insert --invention--.

Column 4, line 42, reads "referably" should read --preferably--.

Column 6, line 37, before "and 2" insert --1--.

IN THE CLAIMS

Column 7, line 47, reads "pas" should read --pass--.

Signed and Sealed this

Twenty-ninth Day of October, 1991

Attest:

HARRY F. MANBECK, JR.

*Attesting Officer*

*Commissioner of Patents and Trademarks*